(12) United States Patent  (10) Patent No.: US 8,257,280 B2
Levin et al.  (45) Date of Patent: Sep. 4, 2012

(54) BIOIMPEDANCE METHODS AND APPARATUS

(75) Inventors: Nathan W. Levin, New York, NY (US); Fansan Zhu, Flushing, NY (US)

(73) Assignee: Renal Research Institute, LLC, New York, NY (US)

( * ) Notice: Subject to any disclaimer, the term of this patent is extended or adjusted under 35 U.S.C. 154(b) by 0 days.

(21) Appl. No.: 13/107,246

(22) Filed: May 13, 2011

(65) Prior Publication Data

US 2011/0275922 A1 Nov. 10, 2011

Related U.S. Application Data

(62) Division of application No. 10/570,368, filed as application No. PCT/US2004/029711 on Sep. 10, 2004, now Pat. No. 7,945,317.

(60) Provisional application No. 60/502,483, filed on Sep. 12, 2003, provisional application No. 60/580,166, filed on Jun. 16, 2004, provisional application No. 60/587,652, filed on Jul. 14, 2004.

(51) Int. Cl.
A61B 5/103 (2006.01)
A61B 5/117 (2006.01)
A61B 5/05 (2006.01)

(52) U.S. Cl. ........................................ 600/587; 600/547

(58) Field of Classification Search .................. 600/306, 600/372, 382, 388, 389, 390, 393, 547, 587; 73/512, 755, 759
See application file for complete search history.

(56) References Cited

U.S. PATENT DOCUMENTS

| 4,008,712 | A | 2/1977 | Nyboer |
| 4,537,203 | A | 8/1985 | Machida |
| 5,068,619 | A | 11/1991 | Nakano et al. |
| 5,335,667 | A | 8/1994 | Cha et al. |
| 5,427,113 | A | 6/1995 | Hiroshi et al. |
| 5,746,214 | A | 5/1998 | Brown et al. |
| 6,088,615 | A | 7/2000 | Masuo |
| 6,125,297 | A | 9/2000 | Siconolfi |
| 6,151,523 | A | 11/2000 | Rosell Ferrer et al. |
| 6,532,384 | B1 | 3/2003 | Fukuda |
| 7,283,869 | B2 * | 10/2007 | Onda et al. ............. 600/547 |
| 2003/0216665 | A1 | 11/2003 | Masuo et al. |
| 2004/0054298 | A1 | 3/2004 | Masuo et al. |

(Continued)

FOREIGN PATENT DOCUMENTS

JP 57-072627 5/1982

(Continued)

OTHER PUBLICATIONS

Bartok, et al., "Estimation of segmental muscle volume by bioelectrical impedance spectroscopy," J Appl Physiol 96:161 166, 2004.

(Continued)

Primary Examiner — Max Hindenburg
Assistant Examiner — Devin Henson
(74) Attorney, Agent, or Firm — Maurice M. Klee

(57) ABSTRACT

Methods and apparatus for providing bioimpedance analysis are provided. In certain aspects, equivalent circuit frequency response models are provided which lead to improved correlations with MRI data. The frequency response models take account of body composition, including the fat component of a body segment. Data obtained by performing bioimpedance spectroscopy (BIS) and MRI on the calves of subjects illustrates the improved correlations achieved compared to single frequency analyses at 50 kilohertz and analyses performed using the conventional Cole-Cole model.

5 Claims, 15 Drawing Sheets

U.S. PATENT DOCUMENTS

2004/0171963 A1      9/2004    Takehara

FOREIGN PATENT DOCUMENTS

| | | |
|---|---|---|
| JP | 01-113645 | 5/1989 |
| WO | WO 02/47548 | 6/2002 |

OTHER PUBLICATIONS

Baumgartner, et al., "Does adipose tissue influence bioelectric impedance in obese men and women?" J Appl. Physiol. vol. 84, pp. 257-262, 1998.

Cole, et al., "Dispersion and absorption in dielectrics. I. Alternating current characteristics" J. Chem. Phys. vol. 9, pp. 341-351, 1941.

Cornish et al., "Data analysis in multiple-frequency bioelectrical impedance analysis," Physiological Measurement, May 1998, 19:275-283.

De Lorenzo, et al., "Predicting body cell mass with bioimpedance by using theoretical methods: a technological review," J Appl Physiol vol. 82, pp. 1542-1558, 1997.

De Lorenzo, et al., "Segmental bioelectrical impedance analysis," Curr Opin Clin Nutr Metab Care 6:551-555, 2003.

Elia, et al., "Modeling Leg Sections by Bioelectrical Impedance Analysis, Dual-Energy X-ray Absorptiometry, and Antrhopometry," Ann. New York Acad. Sci, 904:298-305, 2000.

Foster, et al., "Whole-body impedance—what does it measure?" Am J Clin Nutr vol. 64 (suppl), pp. 388S-396S, 1996.

Fuller, et al., "Predicting composition of leg sections w/ anthropometry & bioelectrical impedance analysis," Clin. Sci, 96:647 657, 1999.

Gudivaka et al., "Single- and multifrequency models for bioelectrical impedance analysis of body water compartments," J Applied Physiology, 1999, 87:1087-1096.

Hanai, T., Electrical properties of emulsions in: Emulsion Science, edited by P.H. Sherman London: Academic, 1968, pp. 354-379.

Kanai et al., "Human Body Impedance for Electromagnetic Hazard Analysis in the VLF to MF Band", IEEE Microwave Theory & Techniques. vol. MTT-32, No. 8, Aug. 1984, p. 763-772.

Janssen, et al., "Estimation of skeletal muscle mass by bioelectrical impedance analysis," J Appl. Physiol, 89:465-471, 2000.

Kamimura et al., "Comparison of skinfold thicknesses and bioelectrical impedance analysis with dual-energy X-ray absorptiometry," Nephrol Dial Transplant, 2003, 18:101-105.

Lukaski, et al., "Validity and Accuracy of Regional Bioelectrical Impedance Devices to Determine Whole-Body Fatness," Nutrition, 19: 851-857, 2003.

Lukaski, H. C., "Regional bioelectrical impedance analysis: applications in health and medicine," Acta Diabetol, 40:S196-S199, 2003.

Miyatani, et al., "Validity of estimating limb muscle volume by bioelectrical impedance," J Appl Physiol, 91:386-394, 2001.

Nyboer, J., Electrical impedance plethysmography, 2nd ed., Charles C. Thomas, Springfield, IL, pp. 28-29, 1970.

O'Brien, et al., "Bioelectrical Impedance to Estimate Changes in Hydration Status," Int J Sports Med, 2002, 23:361-366.

Ohkawa et al., "Standardized thigh muscle area measured by computed axial tomography . . . ," Am J Clin Nutr 71:485-490, 2000.

Patterson, R.P., "Body Fluid Determinations Using Multiple Impedance Measurements," IEEE Engineering in Medicine and Biology magazine. vol. 8, pp. 16-18, 1989.

Piers, et al., "Indirect estimates of body composition are useful for groups but unreliable in individuals," Int J Obes,. 2000 24:1145-1152.

Scharfetter, et al., "Assessing abdominal fatness with local bioimpedance analysis: basics and experimental findings," Int J Obes 25:502-11, 2001.

Schwan, et al., "A dielectric study of the low-conductance surface membrane in *E. coli*," Nature vol. 177, pp. 134-135, 1956.

Schwenk, et al., "Bioelectrical impedance analysis in HIV-infected patients treated with triple antiretroviral treatment," Am J Clin Nutr, 1999, 70:867-873.

Siconolfi, et al., "Assessing total body and extracellular water from bioelectrical response spectroscopy," J Appl Physiol, 1997, 82:704-710.

Thomas, et al., "Bioimpedance spectrometry in the determination of body water compartments: accuracy and clinical significance," Appl Radiat Isot, 1998, 49:447-555.

van den Ham, et al., "Body Composition in Renal Transplant Patients," J Am Soc Nephrol, 10:1067-1079, 1999.

Ward, L. C.,"Inter-instrument comparison of bioimpedance spectroscopic analysers," The Open Medical Devices Journal, 2009, 1:3-10.

Zhu, et al., "Methods and reproducibility of measurement of resistivity in the calf using regional bioimpedance analysis. Blood Purif," vol. 21, pp. 131-136, 2003.

Zhu et al., "An Electrical Resistivity Model of Segmental Body Composition using Bioimpedance Analysis," Proc 25th Int Conf, IEEE EMB, Cancun, Mexico., Sep. 2003, 2679-2682.

Xitron Technologies, Inc., "4000B Bio-Impedance Spectrum Analyzer System Operating Manual," preliminary edition, San Diego, California, 1995, Appendix A, pp. 50-61.

\* cited by examiner

BIOIMPEDANCE METHODS AND APPARATUS

CROSS REFERENCE TO RELATED APPLICATIONS

This application is a division of U.S. application Ser. No. 10/570,368 filed Mar. 2, 2006 now U.S. Pat. No. 7,945,317 which is the U.S. national phase under 35 USC §371 of International Application No. PCT/US2004/29711, filed Sep. 10, 2004, which was published in English under PCT Article 21(2) on Mar. 31, 2005 as International Publication No. WO 2005/027717. The contents of U.S. application Ser. No. 10/570,368 and International Application No. PCT/US2004/29711 are incorporated herein in their entireties This application claims the benefit under 35 USC §119(e) of U.S. Provisional Application No. 60/502,483, filed Sep. 12, 2003, U.S. Provisional Application No. 60/580,166, filed Jun. 16, 2004, and U.S. Provisional Application No. 60/587,652, filed Jul. 14, 2004, the contents of all of which are incorporated herein in their entirety.

FIELD OF THE INVENTION

This invention relates to bioimpedance methods and apparatus and, more particularly, to the use of such methods and apparatus to determine the muscle content, fat content, and/or extracellular fluid content of a segment of the body of a subject, where a segment can include essentially the subject's entire body.

BACKGROUND OF THE INVENTION

The electrical properties of biologic tissue has been of scientific interest for a substantial period time. Many developments and new devices based on a knowledge of bioelectricity have been used in biology and the biomedical area in the last century.

Bioelectrical impedance analysis is one of the interesting and challenging subjects in this area. Bioimpedance has been studied in many areas of medicine because of its potential ability to measure body composition with noninvasive, simple, inexpensive, and portable methods. In particular, bioimpedance has been employed in clinical research for many years. For example, clinical applications using bioimpedance were reported at an early stage by Nyboer [3] and Patterson [4].

Many authors have investigated the nature of the electrical properties of living tissue [2, 4, 5]. Schwan et al. described the relationship between the dielectric properties of the cell membrane using multi-frequency currents [2]. A basic theory to explain electrical properties of tissue in the body has been well established by Cole [1]. In particular, Cole successfully developed an equivalent circuit model (hereinafter the "Cole-Cole model") to explain the electrical response of cells and their membranes to AC current.

A method of using bioimpedance spectroscopy (BIS) has been suggested to measure extracellular (ECV) and intracellular (ICV) fluid volumes based on the Cole-Cole model and the Hanai method [5, 6, 10]. The methodology of multi-frequency bioimpedance analysis can now provide some information about extracellular and intracellular fluid volume in the total or segmental body compartment [6].

However, the accuracy of bioimpedance analysis, including BIS, is a major point of concern by the clinical user [7, 8]. Even though many studies have reported the use of bioimpedance analysis to estimate body fluids, the current techniques have not been accepted widely in clinical practice because of questions regarding reliability, validity, and accuracy.

There are many factors which adversely affect the accuracy of the measurement and analysis using currently available bioimpedance techniques. In accordance with certain of its aspects, the present invention is concerned with one of those factors, namely, the model used to analyze bioimpedance data. The bioimpedance model commonly used to date to calculate electrical properties of different tissues has a basic assumption that fat has a high resistivity compared to fat free mass, and that therefore, fat mass can be ignored. However, a recent study found that bioimpedance measurements at 50 kilohertz are affected when subjects have large amounts of adipose tissue [7]. As discussed in detail below, in accordance with the present invention it has been found that the amount of fat mass is one of the major factors affecting the accurate measurement of body composition by BIS for subjects having a variety of body mass index (BMI) values.

SUMMARY OF THE INVENTION

In accordance with a first aspect, the invention provides a method for analyzing bioimpedance data for a body segment of a subject, said body segment having an external skin surface, said method comprising:

(a) applying alternating current at a plurality of frequencies to at least two points on the external skin surface so as to cause current to pass through the segment;

(b) for each frequency, recording the voltage difference between at least two other points on the external skin surface, said recorded voltage differences comprising both magnitude and phase information (i.e., magnitude and phase values or, equivalently, resistance and reactance values); and (c) using the recorded voltage differences at the plurality of frequencies to determine at least one numerical value indicative of the muscle, fat, and/or extracellular fluid content of the segment, said numerical value being determined using an impedance model for the segment which at least comprises three parallel paths, one of which consists of a capacitor $C_M$ and a resistor $R_I$ in series which represent primarily the muscle component of the segment, one of which consists of a capacitor $C_F$ and a resistor $R_F$ in series which represent primarily the fat component of the segment, and one of which consists of a resistor.

In accordance with a second aspect, the invention provides a method for analyzing bioimpedance data for a body segment of a subject, said body segment having an external skin surface, said method comprising:

(a) applying alternating current at a plurality of frequencies to at least two points on the external skin surface so as to cause current to pass through the segment;

(b) for each frequency, recording the voltage difference between at least two other points on the external skin surface, said recorded voltage differences comprising both magnitude and phase information (i.e., magnitude and phase values or, equivalently, resistance and reactance values); and (c) using the recorded voltage differences at the plurality of frequencies to determine at least one numerical value indicative of the fat and/or extracellular fluid content of the segment, said numerical value being determined using an impedance model for the segment which at least comprises two parallel paths, one of which consists of a capacitor $C_F$ and a resistor $R_F$ in series which represent primarily the fat component of the segment and the other of which consists of a resistor which primarily represents the extracellular fluid component of the segment;

wherein:

(i) the two parallel paths are the only parallel paths of the impedance model which represent the composition of the segment internal to the skin; and (ii) each of the frequencies applied in step (a) is less than or equal to 10 kilohertz.

In accordance with certain embodiments of the foregoing aspects of the invention, a correlation equation is used which transforms a model parameter (e.g., $R_F$) to a physiological value (e.g., a fat content value) for the segment. The correlation equation can be obtained by:

(i) performing steps (a), (b), and (c) on a plurality of calibration subjects to obtain a model parameter value for each of said subjects;

(ii) performing a measurement on the segment for the plurality of calibration subjects (e.g., a measurement of fat content using magnetic resonance imaging) to obtain a physiological value for the segment for each of said subjects; and (iii) performing a regression analysis on the values obtained in steps (i) and (ii) to obtain the correlation equation.

Preferably, the plurality of calibration subjects includes at least one subject having a body mass index less than 20 and at least one subject having a body mass index greater than 35. More preferably, the plurality of calibration subjects includes at least one subject having a body mass index less than 20 and at least one subject having a body mass index greater than 40.

In accordance with a third aspect, the invention provides a method for determining the circumference of a portion of a body segment covered by skin comprising:

(a) applying a series of electrodes around said portion, said series of electrodes having a first electrode and a last electrode, the circumferential distances between all electrodes in the series being known, except for the distance between the first and last electrodes;

(b) determining the resistance between at least two electrodes of the series, other than the first and last electrode, by applying a low frequency current which does not substantially penetrate the skin;

(c) determining a resistivity value per unit length for the skin from the resistance determined in step (b) and the known circumferential distance between the two electrodes;

(d) determining the resistance between the first and last electrodes of the series by applying a low frequency current which does not substantially penetrate the skin; and (e) calculating the distance between the first and last electrodes of the series from the resistance measured in step (d) and the resistivity value per unit length determined in step (c).

It is to be understood that both the foregoing general description and the following detailed description are merely exemplary of the invention, and are intended to provide an overview or framework for understanding the nature and character of the invention.

Additional features and advantages of the invention are set forth in the detailed description which follows, and in part will be readily apparent to those skilled in the art from that description or recognized by practicing the invention as described herein. The accompanying drawings are included to provide a further understanding of the invention, and are incorporated in and constitute a part of this specification.

DETAILED DESCRIPTION OF THE INVENTION AND ITS PREFERRED EMBODIMENTS

Figure 1A:
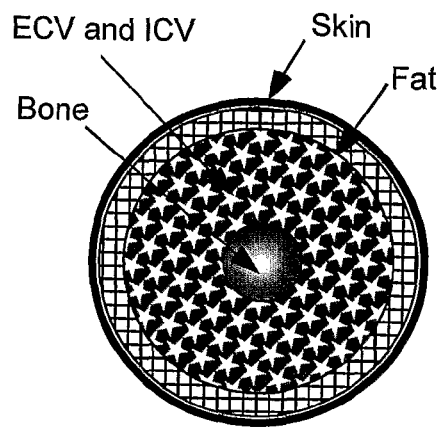
FIG. 1 shows a body composition model in accordance with the invention, both in cross-sectional form (FIG. 1A) and three-dimensional form (FIG. 1B).

As discussed above, the present invention relates to bioimpedance methods and apparatus which can provide information regarding the fat, muscle, and/or extracellular fluid content of a segment of a body of a subject, i.e., a human or an animal.

The segment will typically be a part or all of a subject's limb, e.g., a subject's calf or forearm, but can also be all or part of the subject's torso, e.g., part or all of the subject's abdomen. Similarly, the segment can be as small as a specific muscle or a part of a muscle and as large as essentially the subject's entire body.

The location and size of the segment will depend on the placement of current applying electrodes on the subject's skin. In particular, the segment will constitute the portion of the subject's body through which substantial current passes when the current applying electrodes are activated. By suitable choices of the number, location, and polarity of the current applying electrodes, a variety of current patterns within the subject's body can be achieved. Indeed, by varying the polarity of selected current applying electrodes, more than one segment can be analyzed without the need to move the current applying electrodes.

As known in the art, the potential recording electrodes will typically be located inboard of the current applying electrodes, i.e., the potential recording electrodes will typically be located on skin which surrounds the portion of the patient's body through which substantial current passes when the current applying electrodes are activated.

The application of current and the recording of potentials can be performed with bioimpedance equipment, including current applying and recording electrodes, now known or subsequently developed, e.g., commercially available equipment such as the 4000B Bio-Impedance Spectrum Analyzer System (Xitron Technologies, Inc., San Diego, Calif.) used in the examples discussed below. Alternatively, customized equipment can be used in the practice of the invention.

Processing of the data obtained by the bioimpedance equipment can be performed entirely within the equipment or can be performed on-line using a separate computer. Alternatively, the data can be stored and processed subsequent to the time of measurement.

Preferably, the bioimpedance equipment will include a microprocessor programmed to perform at least a portion of the analysis procedures of the present invention. For example, the bioimpedance equipment can apply a regression equation obtained from a study on calibration subjects to measured impedance data for a subject and thus directly report the subject's fat, muscle, and/or extracellular fluid content(s) to the user of the equipment, e.g., the subject himself and/or other personnel, e.g., a health care provider, interested in the information. The fat, muscle, and/or extracellular fluid content can be reported graphically, numerically (e.g., as a fat and/or muscle percentage value), by color (e.g., red for high fat content), or the like.

In certain embodiments of the invention, alternating current at a plurality of frequencies is applied to the subject's skin. Preferably, at least 10 frequencies are used and more preferably, approximately 50 frequencies are used. Preferably, the plurality of frequencies comprises frequencies between 5 and 1000 kilohertz, although frequencies over larger or smaller ranges can be used if desired. Most preferably, the frequencies are logarithmically distributed over the frequency range.

As discussed above, the bioimpedance model commonly used to date to calculate electrical properties of different tissues has suffered from a number of problems. One of those problems is the basic assumption that fat has a high resistivity compared to fat free mass, and that therefore, fat mass can be ignored. Another is related to the model's calculation of extracellular and intracellular resistances. Although not accounted for in the existing model, that model, which is based on the tissue under the skin, is influenced by the skin and amount of adipose tissue.

The present invention is directed to reducing various of the problems with the present analysis approach by examining the response of different constituent body components, such as skin, fat, muscle, to electrical input. More particularly, the invention, in accordance with certain of its aspects, provides models to describe the effects of different components of body tissue using equivalent circuits.

Specifically, to improve current bioimpedance techniques, in accordance with certain aspects of the present invention, an improved electrical model is provided which is able to explain the electrical properties with different proportions of body tissues, and the effect of a wide range of current frequencies. The data presented below in Example 1 specifically evaluates the relationship of the resistivity at 5 kHz measured at the skin to the resistivity by calculation with the model.

Figure 1B:
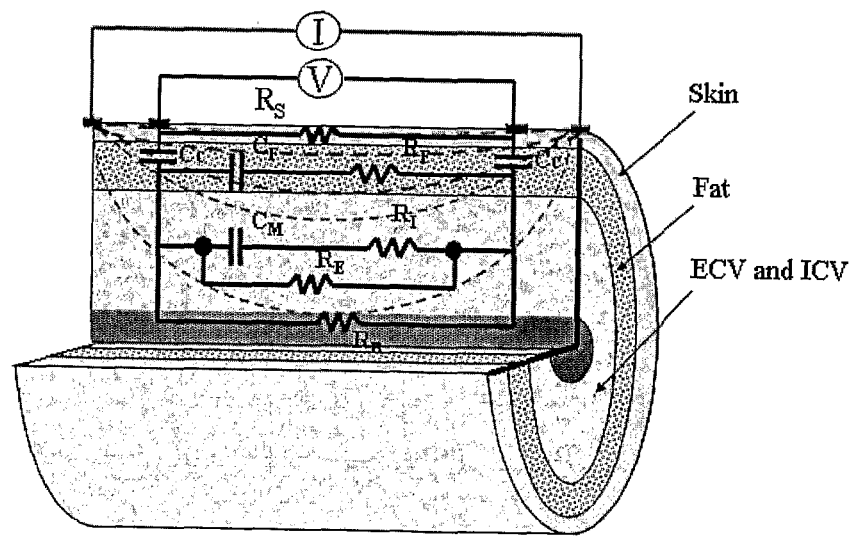

FIG. 1 shows a segmental body composition model in accordance with the invention which can be used to describe the components of conductivity in the limbs. In particular, the figure shows conductive components in a limb segment which form the basis for the electrical models of the invention. For reference, Table 1 shows the electrical properties (permittivity and resistivity) of different tissues using a 10 kHz current frequency as reported in a previous study [8].

Figure 2A:
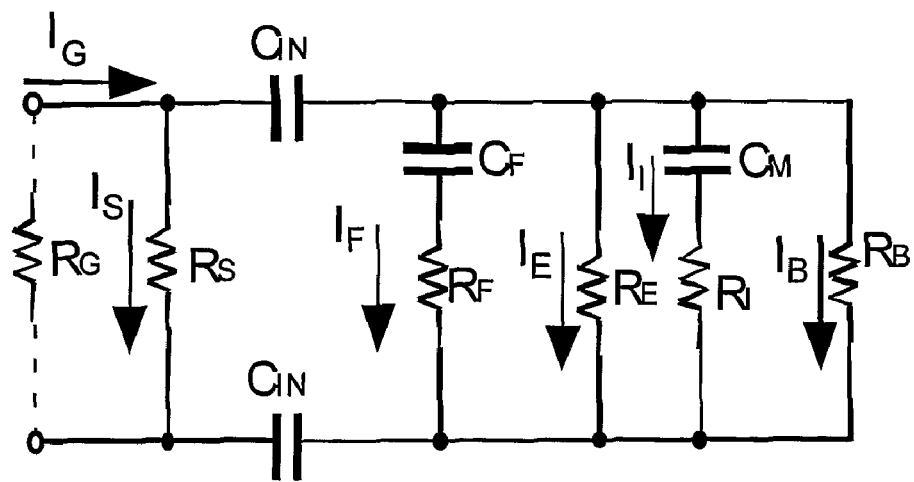
FIGS. 2A and 2B are equivalent circuit frequency response models for the body composition model of FIG. 1.

An equivalent circuit model to FIG. 1 is shown in FIG. 2A, where $R_G$ represents resistance of measurement by two electrodes on the skin and $R_S$, $R_F$, $R_E$, $R_I$, and $R_B$ represent resistance of the skin, fat mass, extracellular volume, intracellular volume, and bone, respectively. In FIG. 2A, $C_{IN}$, $C_F$, and $C_M$ represent capacitance between skin and electrode, capacitance of fat mass, and capacitance of membrane of cells, respectively.

From the model in FIG. 2A, the total electrical current ($I_G$) can be given by:

$$I_G = I_S + I_F + I_E + I_I + I_B \qquad \text{Eq. 1}$$

Potential across $R_G$ can be obtained by:

$$R_G I_G = R_E I_E + \frac{2I'_G}{\omega C_{IN}} \qquad \text{Eq. 2}$$

where $I'_G$ is the current pass through capacitor $C_{IN}$, and is given by:

$$I'_G = I_F + I_E + I_I + I_B \qquad \text{Eq. 3}$$

Because skin resistance ($R_S$) is much higher than in other tissue $I_S$ is very low, so that we have:

$$I'_G \approx I_G \qquad \text{Eq. 4}$$

Figure 3:
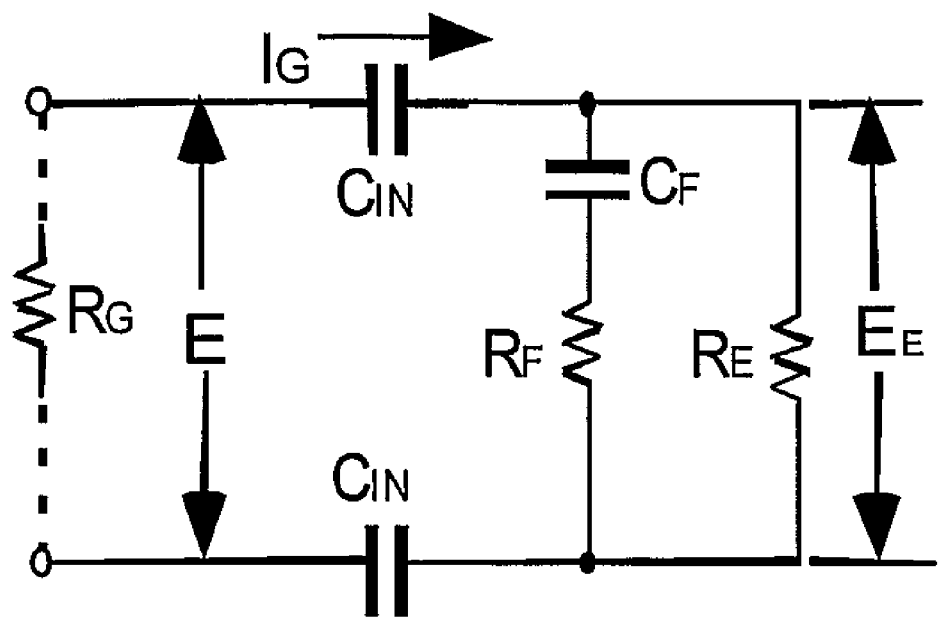
FIG. 3 is an equivalent circuit frequency response model for the body composition model of FIG. 1 under low frequency conditions, e.g., frequencies less than 10 kilohertz.

Since current at low frequency (e.g., 5 kHz) will not pass through the intracellular space, the equivalent circuit can be modified as shown in FIG. 3.

In FIG. 3, E represents the potential between two measuring electrodes (across $R_G$) and $E_E$ represents the potential across $R_E$. Therefore, the following potential equation can be written:

$$E = E_E + \frac{2I_G}{j\omega C_{IN}} \qquad \text{Eq. 5}$$

where the parameter $$\frac{2I_G}{j\omega C_{IN}}$$

represents the potential across the capacitor $C_{IN}$. This potential can be ignored at high current frequency or when $C_{IN}$ is large.

According to the parallel circuit of FIG. 3, the resistance $R_G$ of measurement from skin electrodes can be calculated by:

$$R_G = \frac{R_E\left(\frac{1}{j\omega C_F} + R_F\right)}{R_E + \frac{1}{j\omega C_F} + R_F} + \frac{2}{j\omega C_{IN}} \qquad \text{Eq. 6}$$

Reactance of fat mass ($X_F$) and reactance between skin and electrode ($X_{IN}$) are as follows:

$$X_F = -\frac{j}{\omega C_F}, \quad X_{IN} = -\frac{j}{\omega C_{IN}}$$

Thus, $R_G$ can be simplified to:

$$R_G = R_E\left(1 + \frac{R_E/X_F}{1+(R_E+R_F)/X_F}\right) - 2X_{IN} \qquad \text{Eq. 7}$$

and $$R_G = R_E\left(1 + \frac{A_F}{\frac{\rho_F}{\rho_E}A_E + A_F}\right) - 2X_{IN} \qquad \text{Eq. 8}$$

where $A_F$ and $A_E$ represent the cross sectional area of fat mass from MRI and ECV in this segment, respectively. According to a previous study, the ratio of resistivity in fat mass to resistivity in ECV is approximately as follows [6].

$$\frac{\rho_F}{\rho_K} \approx 3-5 \qquad \text{Eq. 9}$$

Equation 8 can be further simplified to:

$$\rho_G = \rho_E \frac{A_G}{A_E}\left(1 + \frac{A_F}{A_G}\right) - 2X_{IN}\frac{A_G}{L} \qquad \text{Eq. 10}$$

where $\rho_G$ is the resistivity measured on the skin and $\rho_E$ is the resistivity in ECV space with a constant value. Letting $$k_E = \left(1 + \frac{A_F}{A_G}\right) \qquad \text{Eq. 11}$$

and assuming that $$2X_{IN}\frac{A_G}{L}$$

is small, we have:

$$\rho_{G,Cal} = k_E \rho_E \frac{A_G}{A_E} \qquad \text{Eq. 12}$$

If $k_E=1$, resistivity can be calculated by:

$$\rho_{G,Cal}^* = \rho_E \frac{A_G}{A_E} \qquad \text{Eq. 13}$$

The application of these equations and, in particular, Equations 12 and 13 to experimental data obtained from a set of calibration subjects is set forth below in Example 1. The results described therein indicate that the volume of fat mass is an important factor influencing the estimation of body composition using the standard four-electrode bioimpedance technique.

The experimental data of Example 1 was obtained using one frequency for the applied current, namely, 5 kilohertz. The invention's equivalent circuit models of segmental body components are preferably used to describe responses to multi-frequency current. Example 2 shows the results of such multi-frequency testing. In particular, this example shows different decreases in impedance with increases in current frequency for subjects with different fat contents.

Figure 2B:
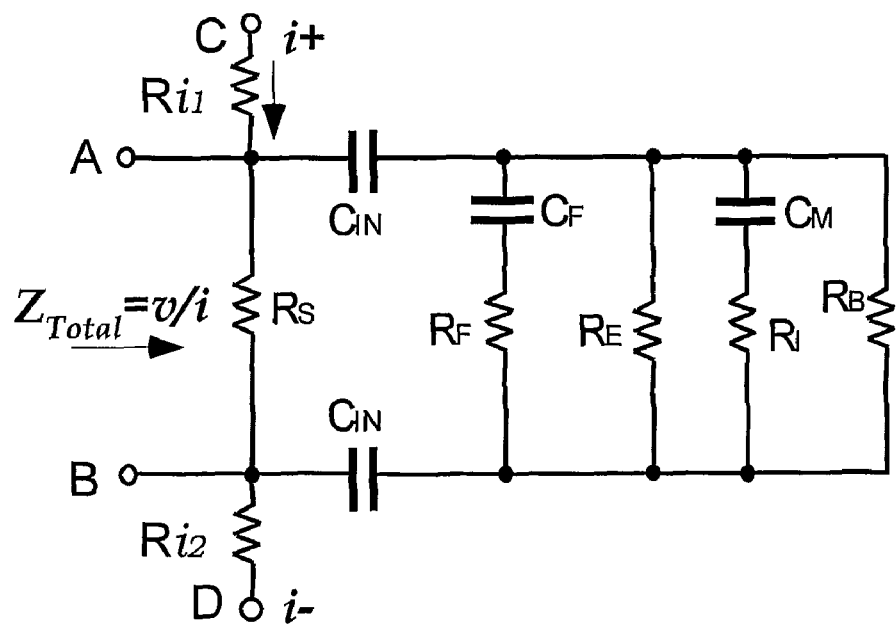

FIG. 2B is a modified version of the equivalent circuit model of FIG. 2A. In FIG. 2B, $Z_{Total}$ represents total impedance of measurement by two electrodes at A and B. As in FIG. 2A, $R_S$, $R_F$, $R_E$, $R_I$, and $R_B$ represent resistance of the skin, fat mass, extracellular and intracellular volume, and bone, respectively, and $C_{IN}$, $C_F$, and $C_M$ represent capacitance between skin and electrode, capacitance of fat mass and the capacitance of the membranes of the cells, respectively. $R_{i1}$ and $R_{i2}$ represent resistance of segmental body between injecting and measuring electrodes.

To obtain a relationship based on frequency for the model of FIG. 2, equations were used to simplify the model so that it can be standardized. First, we let $R_P$ represent the parallel resistance of $R_E$ and $R_B$:

$$R_P = \frac{R_E \times R_B}{R_E + R_B} \qquad \text{Eq. 14}$$

Secondly, we used the following parameters a, b, c, and d to simplify the calculation:

$$a = R_I R_F C_I C_F \qquad \text{Eq. 15}$$

$$b = C_I C_F (R_I + R_F) \qquad \text{Eq. 16}$$

$$c = C_F C_I \qquad \text{Eq. 17}$$

$$d + C_F + C_I \qquad \text{Eq. 18}$$

Total impedance ($Z_{total}$) can be obtained from the circuit of FIG. 2 and is given by the following Eq. 19:

$$Z_{Total} = \frac{\begin{array}{c}aC_{IN}R_P R_S (j\varpi)^3 + \\ R_S[(2+C_{IN})bR_P + 2a](j\varpi)^2 + \\ R_S[(C_{IN}cR_P + 2b + 2dRp)(j\varpi) + 2cR_S\end{array}}{\begin{array}{c}C_{IN}[R_S(a+bR_P)+aR_P](j\varpi)^3 + \\ [R_S C_{IN}(dR_P+b)+bR_P(2+C_{IN})+2a](j\varpi)^2 + \\ [cR_S C_{IN}+(cC_{IN}+2d)R_P+2b)(j\varpi)+2c\end{array}} \qquad \text{Eq. 19}$$

To standardize Eq. 19, we let $$\mu = C_{IN}[R_S(a+bR_P)+aR_P] \qquad \text{Eq. 20}$$

$Z_{Total}$ is then given by Eq. 21 as follows:

$$Z_{Total} = \frac{\left(\frac{1}{\mu}\right)aC_{IN}R_P R_S(j\varpi)^3 + \frac{1}{\mu}R_S[(2+C_{IN})bR_P + 2a](j\varpi)^2 + \frac{R_S}{\mu}[(C_{IN}cR_P + 2b + 2dR_P)](j\varpi) + \frac{2cR_S}{\mu}}{(j\varpi)^3 + \frac{1}{\mu}\left[\begin{array}{c}R_S C_{IN}(dR_P+b)+\\ bR_P(2+C_{IN})+2a\end{array}\right](j\varpi)^2 + \frac{1}{\mu}[cR_S C_{IN} + (cC_{IN}+2d)R_P + 2b)](j\varpi) + \frac{2c}{\mu}} \quad \text{Eq. 21}$$

Quantitative analysis of frequency response data for individual subjects is preferably performed using a group of parameters to represent the function of components in the equivalent circuit. Such a group of parameters helps in the identification of differences in the body composition of individual subjects by facilitating the use of a standard transfer function for the analysis.

Equation 21 can, for example, be normalized using the following relationship, where $P_1, P_2, P_3, P_4, Q_1, Q_2, Q_3$ are the group of parameters:

$$Z_{Total} = \frac{P_1(j\varpi)^3 + P_2(j\varpi)^2 + P_3(j\varpi) + P_4}{(j\varpi)^3 + Q_1(j\varpi)^2 + Q_2(j\varpi) + Q_3} \quad \text{Eq. 22}$$

Values for $R_I, R_F, C_I, C_F, R_P, R_S, C_{IN}$ for individual patients (individual subjects) are calculated using the following equations:

$$P_1 = \left(\frac{1}{\mu}\right)aC_{IN}R_P R_S \quad \text{Eq. 23}$$
$$= \frac{aC_{IN}R_P R_S}{C_{IN}[R_S(a+bR_P)+aR_P]}$$
$$= \frac{aR_P R_S}{R_S(a+bR_P)+aR_P}$$

$$P_2 = \frac{1}{\mu}R_S[(2+C_{IN})bR_P + 2a] \quad \text{Eq. 24}$$
$$= \frac{R_S[(2+C_{IN})bR_P + 2a]}{C_{IN}[R_S(a+bR_P)+aR_P]}$$

$$P_3 = \frac{R_S}{\mu}[C_{IN}cR_P + 2b + 2dR_P] \quad \text{Eq. 25}$$
$$= \frac{R_S[C_{IN}cR_P + 2b + 2dR_P]}{C_{IN}[R_S(a+bR_P)+aR_P]}$$

$$P_4 = \frac{2cR_S}{\mu} = \frac{2cR_S}{C_{IN}[R_S(a+bR_P)+aR_P]} \quad \text{Eq. 26}$$

$$Q_1 = \frac{1}{\mu}[R_S C_{IN}(dR_P+b) + bR_P(2+C_{IN}) + 2a] \quad \text{Eq. 27}$$
$$= \frac{[R_S C_{IN}(dR_P+b) + bR_P(2+C_{IN}) + 2a]}{C_{IN}[R_S(a+bR_P)+aR_P]}$$

$$Q_2 = \frac{1}{\mu}[cR_S C_{IN} + (cC_{IN} + 2d)R_P + 2b)] \quad \text{Eq. 28}$$
$$= \frac{[cR_S C_{IN} + (cC_{IN} + 2d)R_P + 2b)]}{C_{IN}[R_S(a+bR_P)+aR_P]}$$

$$Q_3 = \frac{2c}{\mu} = \frac{2c}{C_{IN}[R_S(a+bR_P)+aR_P]]} \quad \text{Eq. 29}$$

where a, b, c, and d are as defined above in Equations 15-18.

In these equations, $R_I, R_F, C_I, C_F, R_P, R_S, C_{IN}$ are the variables to be determined and $P_1, P_2, P_3, P_4, Q_1, Q_2, Q_3$ are data values for an individual patient obtained by curve fitting of the frequency response data for the patient. In particular, the values of the seven variables $R_I, R_F, C_I, C_F, R_P, R_S, C_{IN}$ for an individual patient are obtained by solving the above seven equations (Eq. 23 to Eq. 29) using the $P_1, P_2, P_3, P_4, Q_1, Q_2, Q_3$ values for that patient.

In Example 2 below, the curve fitting program of the MATLAB toolbox (The MathWorks, Inc., Natick, Mass.) was used to obtain the values of the parameters $P_1, P_2, P_3, P_4, Q_1, Q_2, Q_3$ for individual patients. Simulation of frequency response curves was obtained using the standard signal processing program of the MATLAB toolbox.

Although Eq. 22 is a preferred curve fitting equation for use with the type of frequency response data obtained during a bioimpedance experiment, as will be evident to persons skilled in the art from the present disclosure, other curve fitting equations can be used if desired. Similarly, other math processing programs besides the MATLAB programs can be used in the practice of the invention.

Segmental length and circumference can be measured manually. Alternatively, in accordance with certain embodiments of the invention, the circumference and the length of a segment can be measured using groups of electrodes instead of single electrodes (see FIG. 4). The resistance at low frequency (e.g., <10 Hz, preferably <1 Hz) can reflect the electrical properties of the skin. Since the distance between any adjacent two electrodes in each pair is known, the circumference of the measurement area can be calculated as, $$C = D \cdot (n-1) + \frac{R_n}{\lambda} \quad \text{Eq. 30}$$

where C represents the circumference, n is the number of electrodes, D is a known distance between two adjacent electrodes, $R_n$ (n=8 in FIG. 5) is the resistance between the first and last electrode when the electrodes form a circle on any segment, and $\lambda$ is the ratio of resistivity to the area of cross sectional area which can be calculated by $$\lambda = \frac{1}{n-1}\sum_{i=1}^{n-1}\frac{R_i}{D_i} \quad \text{Eq. 31}$$

where $R_i$ is the resistance between any adjacent two electrodes except the resistance between the first and end, $D_i$ is the distance between any adjacent two electrodes except the distance between the first and the last electrodes.

Thus, specific resistivity in skin of this segment is $$\rho' = \lambda \times A \quad \text{Eq. 32}$$

where A is the cross sectional area in the segment. Since $A = C^2/(4*\pi)$, $\rho'$ can be calculated by $$\rho' = \lambda * C^2/(4*\pi) \quad \text{Eq. 33}$$

Once the skin resistivity is determined, the length can be calculated by the equation $$L = A * R_L / \rho' \quad \text{Eq. 34}$$

where L is the length and A is the cross sectional area of the segment and $R_L$ is the resistance between two cross sectional areas along the vertical axis of the segment.

Figure 4:
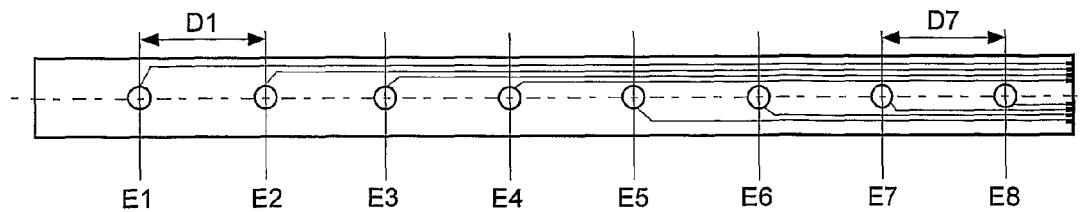
FIG. 4 shows an electrode configuration that can be used in the practice of the invention.
Figure 5:
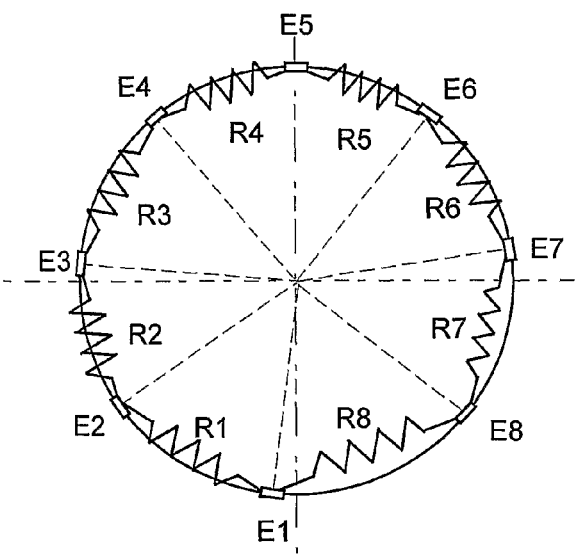
FIG. 5 shows a resistor model for the electrode configuration of FIG. 4.

In FIG. 4, E1 to E8 are electrodes, D1 to D7 represent the distance between two adjacent electrodes respectively, and D1=D2= . . . =D7. In FIG. 5, R1 to R7 represents the skin resistance between adjacent two electrodes. R8 is the resistance between, as discussed above, the first (E1) and the last electrode (E8). The distance between E1 and E8 is unknown but it, as discussed above, can be calculated by R8/λ and therefore, the circumference (C) can be calculated by Eq. 30.

The mathematical operations described herein can be performed using a variety of computers and software. For example, those operations can be performed using the commercially available MATLAB program discussed above and a personal computer configured to run that program in accordance with the program manufacturer's specifications. The program as customized to perform the mathematical operations of the invention can be embodied as an article of manufacture comprising a computer usable medium, such as a magnetic disc, an optical disc, or the like, upon which the program is encoded. The data generated by the programs can similarly be stored on various types of storage media.

Without intending to limit it in any manner, the present invention will be more fully described by the following examples.

Example 1

Effect of Fat Mass on Bioimpedance Analysis

This example shows that fat mass is a major factor affecting the accurate measurement of body composition, including the accurate measurement of body fluid in clinical practice in dialysis patients, using bioimpedance analysis.

28 chronic hemodialysis patients were studied before treatment. Table 2 sets forth the relevant parameters for this group of subjects (patients).

Figure 6:
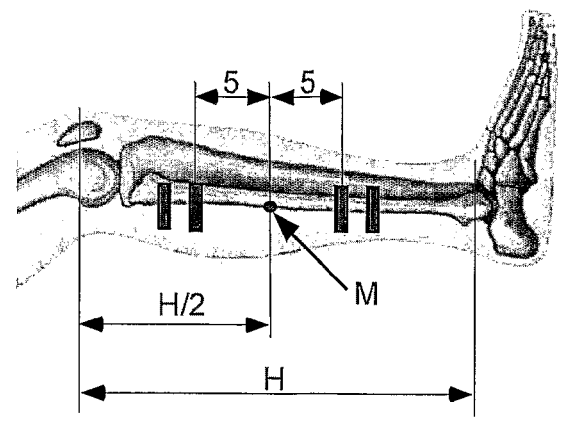
FIG. 6 shows the electrode placement used to generate the bioimpedance data of the examples presented below.

Calf bioimpedance measurements were performed using BIS device Xitron 4200 (Xitron Technologies, San Diego, Calif.). The procedure of placement of electrodes was published in a previous study [9]. As described therein, to place the electrodes in the normal position, the distance (H) between the central part of the patella and the center of the lateral malleolus was measured while the subject was in the sitting position (see FIG. 6). With the patient recumbent, two measuring electrodes were placed, one 5 cm above the mid point M and another 5 cm below. Two current injecting electrodes were placed, one 3 cm above and the other 3 cm below the measuring electrodes. The circumference of the calf at the two measuring electrodes was measured using a tape with 0.1 cm precision.

Calf resistance and reactance were measured using the BIS device with 50 logarithmically distributed frequencies from 5 kHz to 1 MHz. Extracellular resistance (Re) and intracellular resistance (Ri) were calculated and ECV and ICV were obtained using a program provided by the BIS device [9, 10]. Fat mass, muscle mass, and bone were separately measured in the same area by MRI.

Geometric volume ($V_G$) was defined as the cross sectional area ($A_G$) times the length (L) of the segment. $A_G$ can be calculated by $A_G = C^2/(4\pi)$, where C is average value of circumferences in the calf. Resistivity ($\rho_{G,Mea}$) was calculated by the value of measurement shown as follows:

$$\rho_{G,Mea} = \frac{R_G \times A_G}{L} \quad \text{Eq. 35}$$

where $R_G$ is resistance measured at 5 kHz, $A_G$ is cross sectional area and length was fixed at 10 cm for all subjects.

In order to compare the effect of volume of fat mass on the value of resistivity from both measurement and calculation, the 28 patients were divided into two groups according to the ratio of fat mass ($V_F$) to geometric volume ($V_G$): the high fat group was defined as $V_F/V_G > 0.2$ and the normal fat group was defined as $V_F/V_G \leq 0.2$. Data is presented as mean value±SD, and the student t-test was used to compare the data from different groups. A difference between groups was considered significant if the p value<0.05.

Table 3 shows results of comparison of the resistivity between the two groups. There were significant differences in $\rho_{G,Mea}$ (p<0.05), $\rho_{G,Cal}$ (p<0.005) and Δρ (p<0.05), however, no significant difference was seen in $\rho^*_{G,Cal}$ between the two groups (Table 3). The difference (p<0.05) between $\rho_{G,Mea}$ and $\rho^*_{G,Cal}$ was significant but no significant difference was seen between $\rho_{G,Mea}$ and $\rho_{G,Cal}$.

Figure 7:
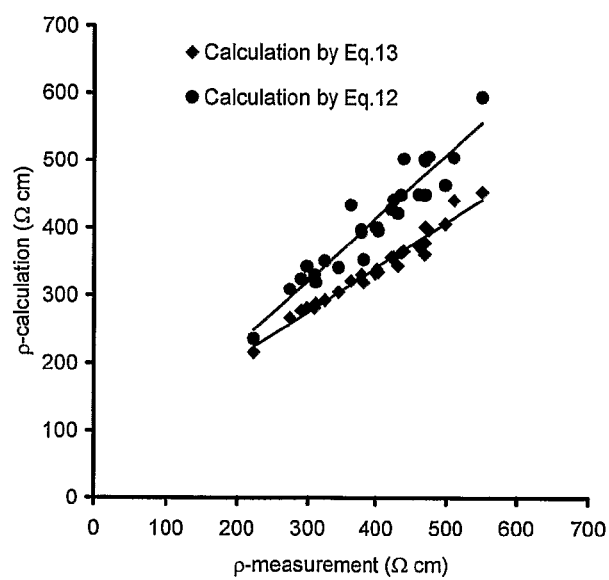
FIG. 7 shows correlations between measured and calculated p values obtained using Equations 12 and 13. The steeper slope of the correlation obtained using Equation 12 illustrates the value of including information regarding fat content in equivalent circuit frequency response models for bioimpedance measurements.

FIG. 7 shows correlations between calculated and measured resistivity values using Equations 12 and 13. The figure shows a high degree of correlation between the resistivity ($\rho_{G,Mea}$) determined from Eq. 35 which is based on the measured value and the resistivity ($\rho_{G,Cal}$) calculated using Eq. 12. In FIG. 7, the diamond symbols represent the correlation of $\rho_{G,Mea}$ with $\rho^*_{G,Cal}$ by Eq. 13 ($\rho^*_{G,Cal} = 0.66\rho_{G,Mea} + 76.7$, $R^2 = 0.96$) and the symbols of solid circles represent the correlation between $\rho_{G,Mea}$ and $\rho_{G,Cal}$ with individual various $k_E$ calculated by Eq. 12 ($\rho_{G,Cal} = 0.93\rho_{G,Mea} + 41.1$, $R^2 = 0.9$). Even though the correlation is high between $\rho^*_{G,Cal}$ and $\rho_{G,Mea}$, the slope (diamond symbol) is only 0.66. After calibration with individual $k_E$ using Eq. 12, the slope is 0.93 (solid circles), i.e., significantly better.

Knowledge of the relationship of resistivity measured at the skin to the various subcutaneous tissues is essential to understand the relevant bioelectric phenomena. Many early studies have shown the resistivity of various biologic tissues and organs by direct measurement [6]. However, since clinical measurements are performed on the surface of skin and the resistivity of different tissues is calculated by a number of theoretical models, errors may occur due to: (1) individual different impedance interfaces of electrode and skin; (2) different volumes of adipose tissue between individuals and (3) theoretical models that do not include the variables of differences in skin impedance and fat mass between individuals.

The present invention provides a model which includes the variable of impedance of fat mass and may include the variables of resistance of skin and interface between capacitance. Table 3 shows that there is significant difference in resistivity (Δρ) at 5 kHz between calculation by the model and by measurement as the amount of fat mass increases. This suggests that the value of resistivity at low frequency (5 kHz) obtained from measurement on the skin should include the contribution not only from extracellular fluid compartment but also from the fat mass compartment. FIG. 7 shows that after calibration with individual $k_E$ the slope of the curve as shown by the solid circles is almost equal to one, which indicates that the calculated value is close to the measurement values. It is important to understand that the variability of resistivity in healthy subjects depends mainly on the individual volume of fat mass. Therefore using this model, correct information concerning ECV can be obtained by measurement of, for example, calf resistivity. This information is important to provide, among other things, an accurate parameter of hydration for adjusting the variably abnormal hydration in dialysis patients; this will permit targeting appropriate body weight by removal of excess body fluid during dialysis.

In summary, this example illustrates some of the aspects of the invention that provide a model which can be used as a basis to calculate the resistivity in different tissues from the measurement of resistivity at the skin surface. That is, this example illustrates some of the aspects of the invention that provide an electrical resistivity model of segmented body composition for use in bioimpedance analysis, where the model describes the relationship of the resistivity with measurement on the skin surface and by calculation of tissues composing a limb.

In particular, in this example, a specific analysis was performed in a group of subjects with 5 kHz current injected at the surface of the calf. The study showed that calculated resistivity using the model was highly correlated with the values of resistivity by actual measurement. In the next example, the response of the system to current of different frequencies is investigated. The results of that example show that the resistivity of cell membranes can be tested using the three parallel path model of the invention.

Example 2

Multi-Frequency Analysis

To improve existing BIS techniques, a correct electrical model should be able to explain the electrical properties with different proportions of body tissues over a wide range of current frequencies. The aim of this study was to evaluate frequency response of the equivalent circuit model from 5 kHz to 1 MHz measured at the skin of the calf. The equivalent circuit model is shown in FIG. 2B.

The same 28 chronic hemodialysis patients as in Example 1 were studied before treatment (see Table 2). Again, calf bioimpedance measurements were performed using BIS device Xitron 4200 (Xitron Technologies, San Diego, Calif.) and the placement of electrodes was as described above in Example 1 (see FIG. 6).

Calf resistance and reactance were measured using BIS device with 50 logarithmically distributed frequencies from 5 kHz to 1 MHz. Fat mass, muscle mass and bone were separately measured in the same area of BIS measurement by MRI. Patients were divided into three groups according to the amount of fat mass in the calf with G1: fat>0.4 kg, G2: 0.25<fat<0.4 kg and G3: fat<0.25 kg.

Figure 8:
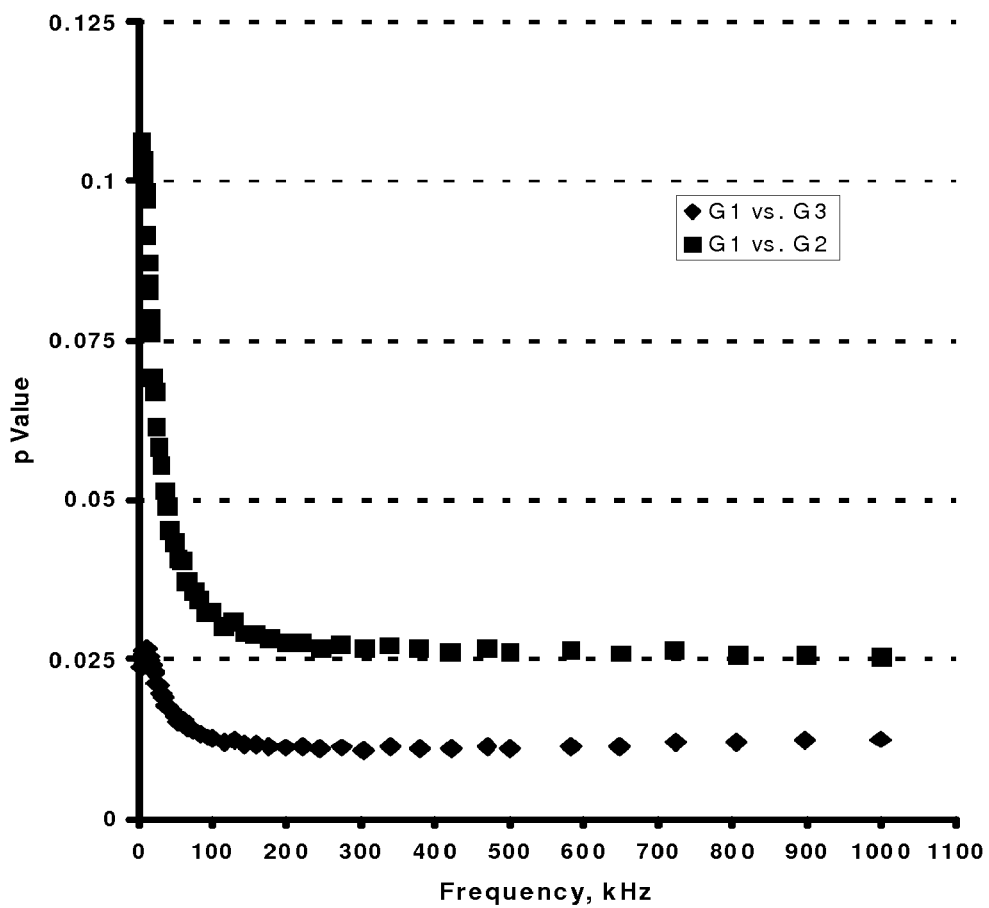
FIG. 8 shows p values of a t-test between groups of subjects having different fat contents.
Figure 9:
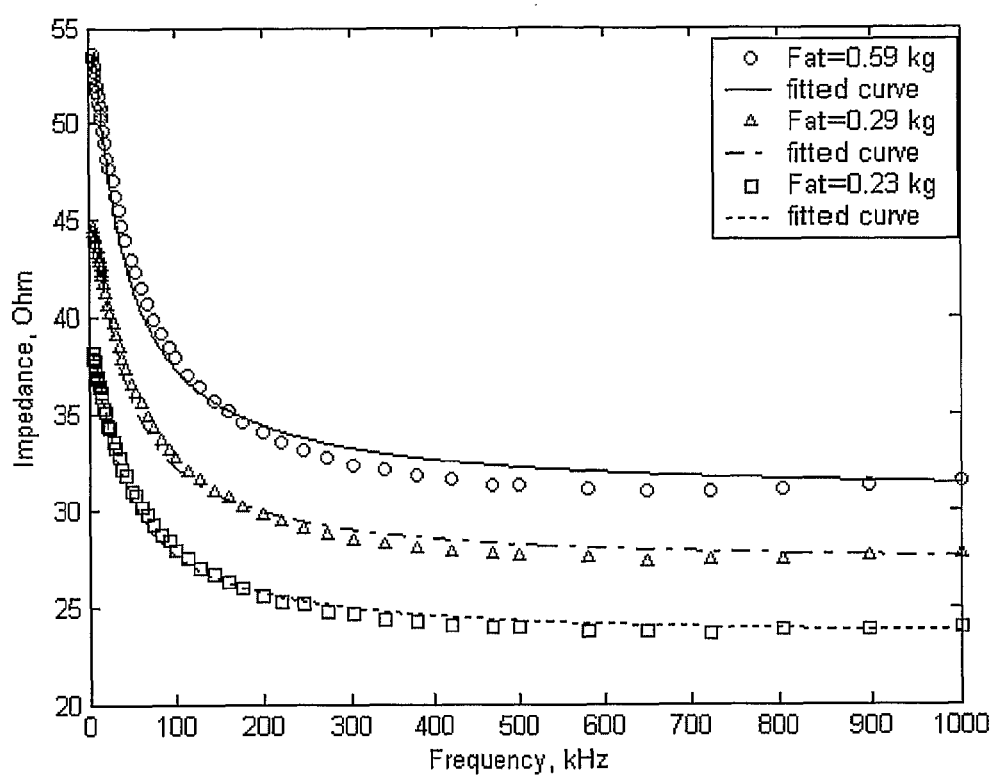
FIG. 9 shows curve fitting of impedance for three subjects (patients) having different fat contents.

Significant differences in resistance, reactance and impedance between G1 and G3 were found; however, the significant difference between G1 and G2 show only with frequencies higher than 40 kHz (FIG. 8). Results of curve fitting to the raw data (circle, triangle and square) of impedance with different frequencies are shown in FIG. 9. The data shown by circles is for a patient having a fat mass of 0.59 kg as estimated by MRI, while the triangles and squares show data for two other patients having fat masses of 0.29 kg and 0.23 kg, respectively, again estimated by MRI.

Figure 10A:
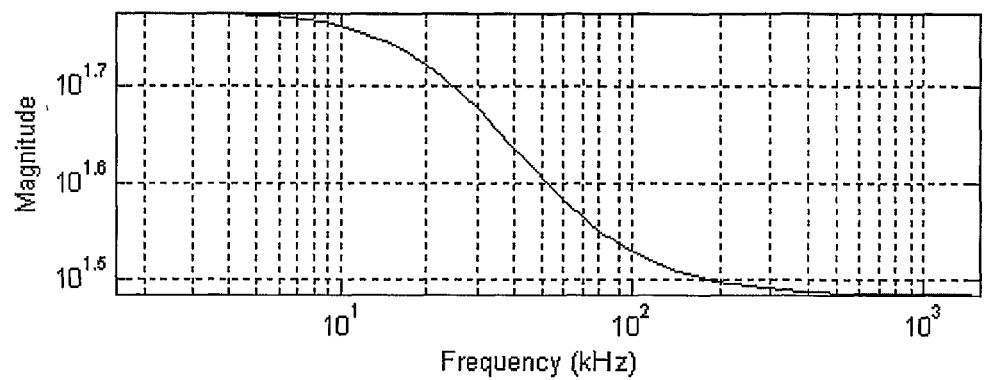
FIG. 10 shows impedance magnitude (FIG. 10A) and impedance phase (FIG. 10B) for a subject (patient) with a 0.588 kg fat mass.
Figure 10B:
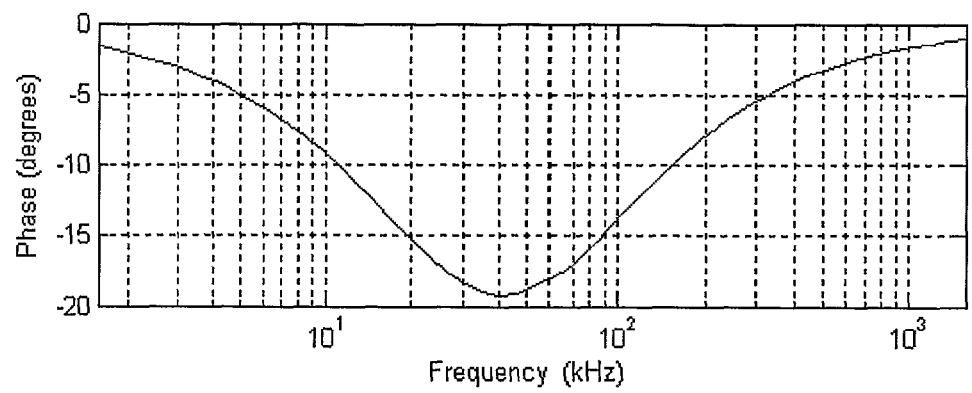
Figure 11A:
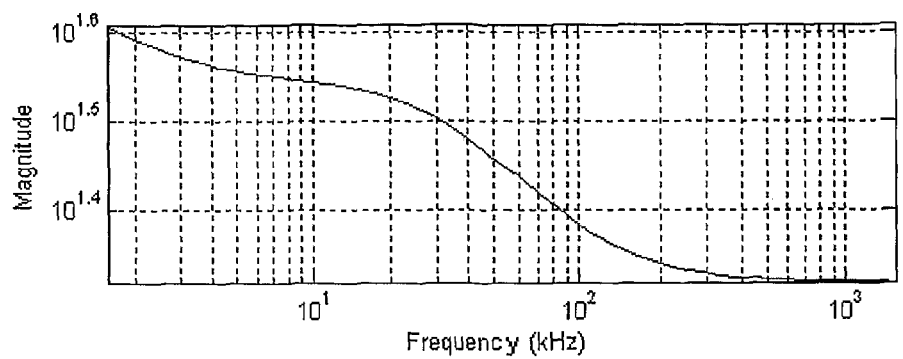
FIG. 11 shows impedance magnitude (FIG. 11A) and impedance phase (FIG. 11B) for a subject (patient) with a 0.134 kg fat mass.
Figure 11B:
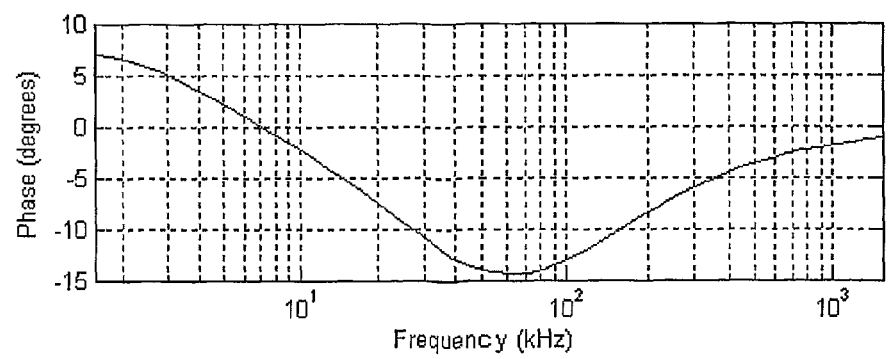

The frequency response curve (A) and phase response (B) are shown in FIGS. 10 and 11 from two patients: one had 0.55 kg fat mass, 1.046 kg muscle mass and 0.021 kg bone (FIG. 10) as estimated by MRI and the other had 0.134 kg fat mass, 1.022 kg muscle mass and 0.022 kg bone (FIG. 11), again estimated by MRI.

It is clearly observed that impedance of the patient with smaller fat mass decreases in the range of frequency from 1 to 10 kHz (FIG. 11A), however, the curve is almost constant in the same frequency range when patient has a larger fat mass (FIG. 10A). In addition, at the minimum point of phase, the magnitude of the frequency is different between the two patients.

Figure 12:
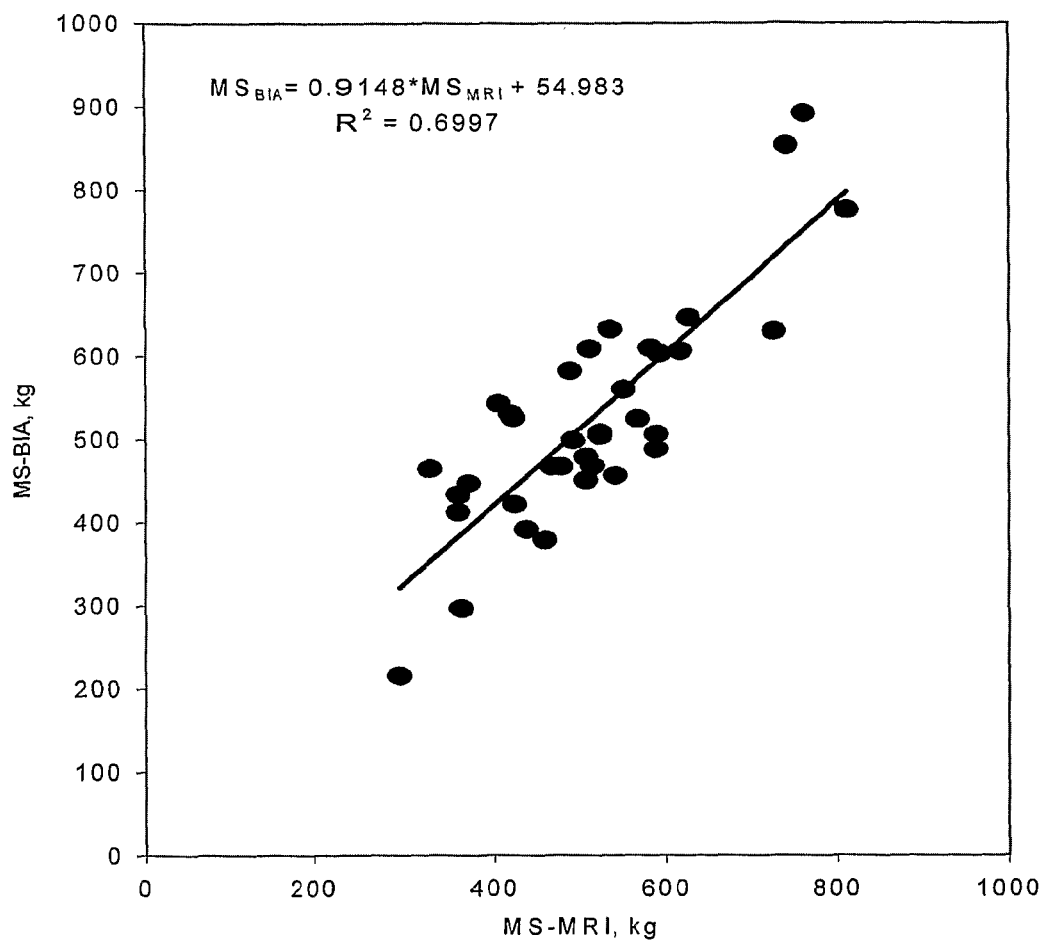
FIG. 12 shows a correlation between muscle (MS) estimation by MRI and by a BIS technique of the invention.

FIG. 12 shows a correlation of muscle (MS) estimation by BIS and by MRI ($MS_{BIS}=285*L^2/Ri$, where L (10 cm) is the distance between measuring electrodes along the patient's calf and Ri is intracellular resistance which was calculated using the model of FIG. 2B). The value of 285 $\Omega$-cm used as muscle resistivity in calculating $MS_{BIS}$ was obtained by a regression analysis based on the MRI data.

In generating FIG. 12, for each patient, Ri was determined by solving Equations 23-29 using the $P_1$, $P_2$, $P_3$, $P_4$, $Q_1$, $Q_2$, and $Q_3$ values obtained for that patient from the measured frequency response data. FIG. 12 thus illustrates the use of a group of parameters to quantify the analysis of the frequency response of the components of an equivalent circuit which can be used to identify the differences in body composition of individual subjects.

Differences in $P_1$, $P_2$, $P_3$, $P_4$, $Q_1$, $Q_2$, and $Q_3$ values were investigated for groups G1, G2, and G3 discussed above. Table 4 shows the significant difference (p<0.05) of $P_1$ between G1 and G2 and the significant difference of $P_4$ between G1 and G3. There were no significant differences except for $P_i$ and $P_4$ in the P and Q parameters.

Example 1 above showed that electrical resistivity of measurement on the skin surface is affected by adipose tissue using the equivalent circuit model of FIG. 2. This is believed to be one of the more important factors which influence the accuracy of bioimpedance technique to estimate body composition such as extracellular and intracellular fluid volumes. Of course, bioimpedance accuracy is not only influenced by the amount of fat mass but also by the interface between electrodes and skin or the degree of skin hydration.

In this example, the results shown in FIG. 9 demonstrate a decrease in impedance related to increase of the current frequency in patients with different fat content. Impedance of the patient with larger fat mass is higher than that of the patient with small fat mass. Simulation results of two patients with similar muscle mass and bone mass show that the frequency response curve is different in the frequency range from 0 to 1 kHz. The difference between FIGS. 10 and 11 demonstrate that the change in curve in response to the frequency from 0 to 1 kHz depends on the fat mass and that will largely affect the estimation of extracellular and intracellular resistance by multi-frequency bioimpedance analysis. Moreover, the difference at the minimum point of phase response between the two patients indicates that using 50 kHz single frequency bioimpedance method could produce error when subject has a larger fat mass.

The correlation between muscle estimation by BIS and by MRI shown in FIG. 12 has a number of important implications for clinical and other applications. Thus, as illustrated in this figure, the electrical model of the present invention correlates well with actual muscle mass as measured by MRI. The model therefore allows one to determine the muscle mass of individual subjects (patients) using only simple, inexpensive, and non-invasive electrical measurements.

The particular muscle mass determined using the model will depend on the particular locations chosen for the electrodes used to make the BIS measurement. For example, the data of FIG. 12 is for the entire calf muscle. By using a different electrode placement, the muscle mass of, for example, a portion of the calf muscle can be determined, e.g., the muscle mass of the gastrocnemius portion of the calf. Alternatively, rather than making measurements on the calf muscle, measurements can be made on other muscles, portions of muscles, and/or or muscle groups, e.g., measurements can be made on all or part of a subject's biceps. If only relative measurements are needed, the bioimpedance measurement can be used as is. Alternatively, correlations of the type shown in FIG. 12 can be obtained between bioimpedance measurements and MRI measurements for particular muscles, portions of muscles, or muscle groups, thus allowing the electrical measurements to provide "absolute" values for muscle mass, where "absolute" values are preferably those which correspond to those obtained using MRI, the acknowledged "gold standard" for muscle mass measurements.

The ability to measure muscle mass, discrete muscles or muscle groups with suitable application of electrodes, with or without validation against MRI measurements, has numerous applications. For example, these techniques are applicable in exercise programs in the home, gymnasium, sports and health clubs and in rehabilitation after surgery and injury, where the effect of muscle mass increases is relevant. Thus, by taking a series of bioimpedance measurements over time, subjects (patients) and/or their health care professionals can monitor changes in muscle mass as a result of exercise programs, diet changes, and/or rehabilitation programs.

Example 3

Single Low Frequency Bioimpedance Measurements

Figure 13:
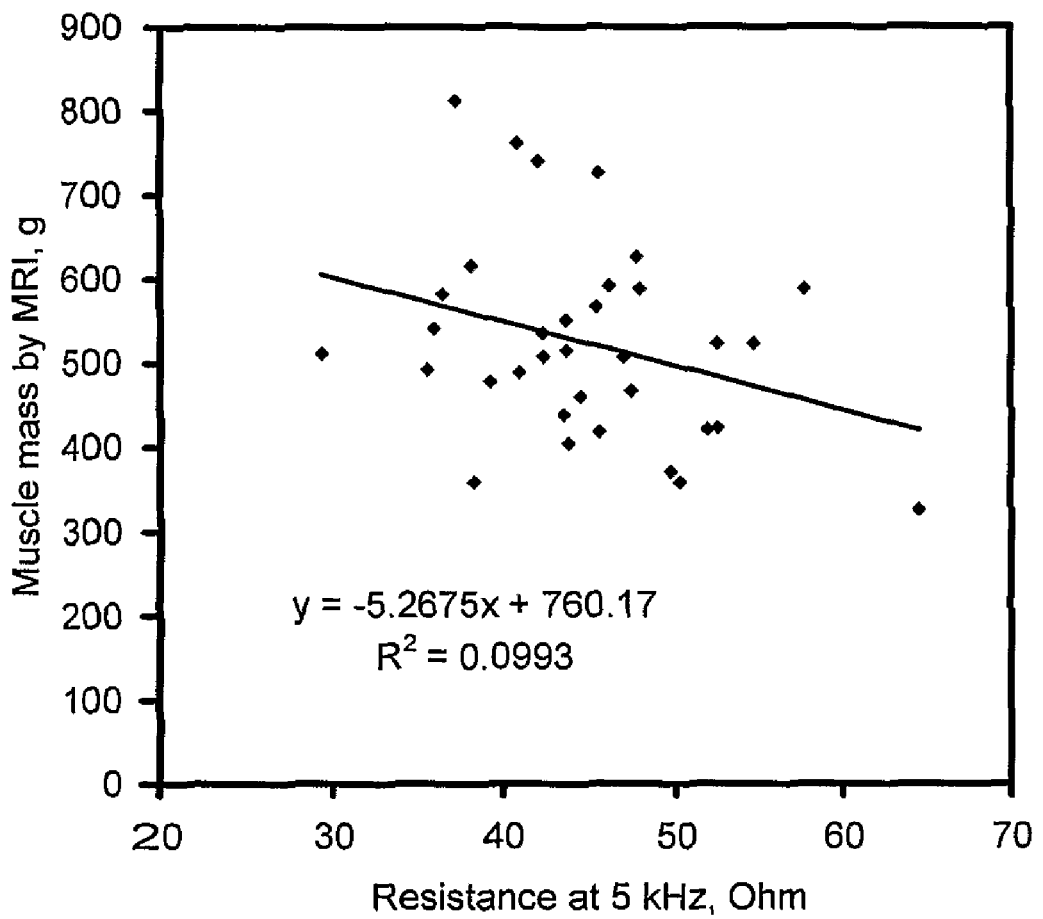
FIG. 13 shows a correlation between muscle mass measured by MRI and resistance measured at 5 kHz.

FIG. 13 is a plot based on the data of Examples 1 and 2 which shows the lack of a correlation between measured resistance values at 5 kilohertz and muscle mass determined by MRI. This data supports the conclusion that at low frequencies, measured bioimpedance data is not responsive to the muscle content of a segment. Rather, as set forth in the circuit model of FIG. 3, at these frequencies, the components of a segment that primarily determine the measured values obtained with a bioimpedance procedure are the fat and extracellular fluid components.

Example 4

Figure 14A:
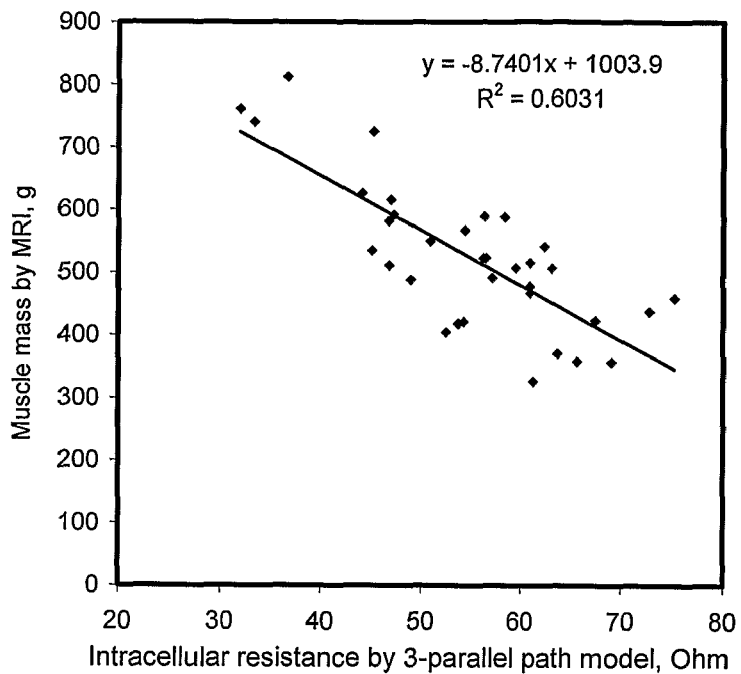
FIG. 14 compares (i) a correlation between muscle mass measured by MRI and intracellular resistance ($R_I$) determined using the multi-frequency, three parallel path model of the invention (FIG. 14A) with (ii) a correlation between muscle mass measured by MRI and impedance at 50 KHz (FIG. 14B).
Figure 14B:
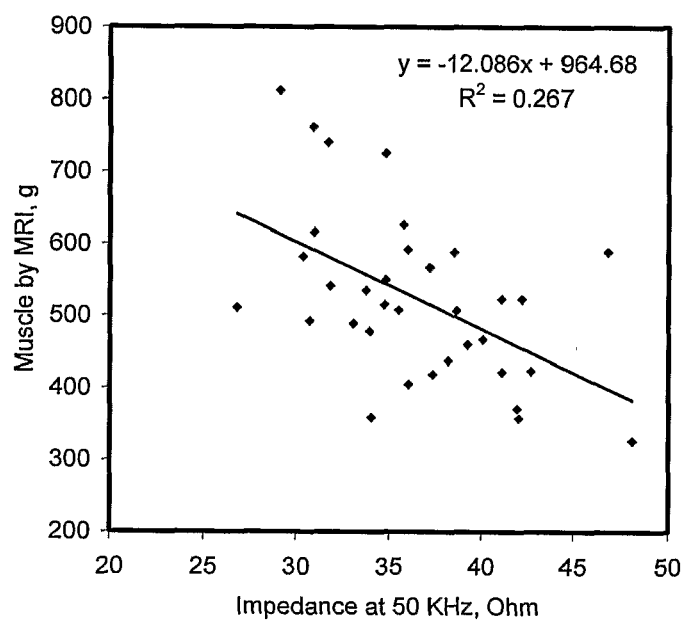
Figure 15A:
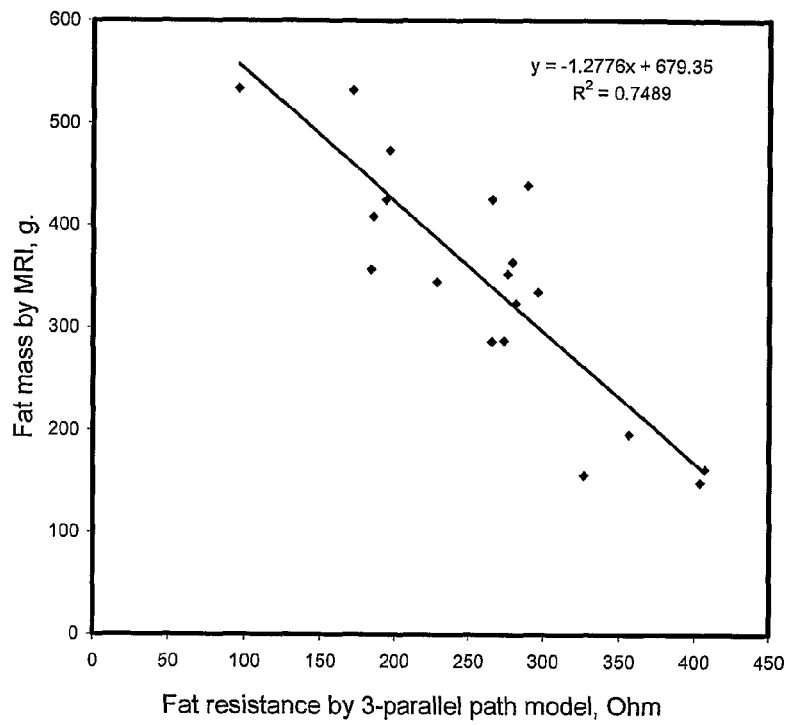
FIG. 15 compares (i) a correlation between fat mass measured by MRI and fat resistance ($R_F$) determined using the multi-frequency, three parallel path model of the invention (FIG. 15A) with (ii) a correlation between fat mass measured by MRI and impedance at 50 KHz (FIG. 15B).
Figure 15B:
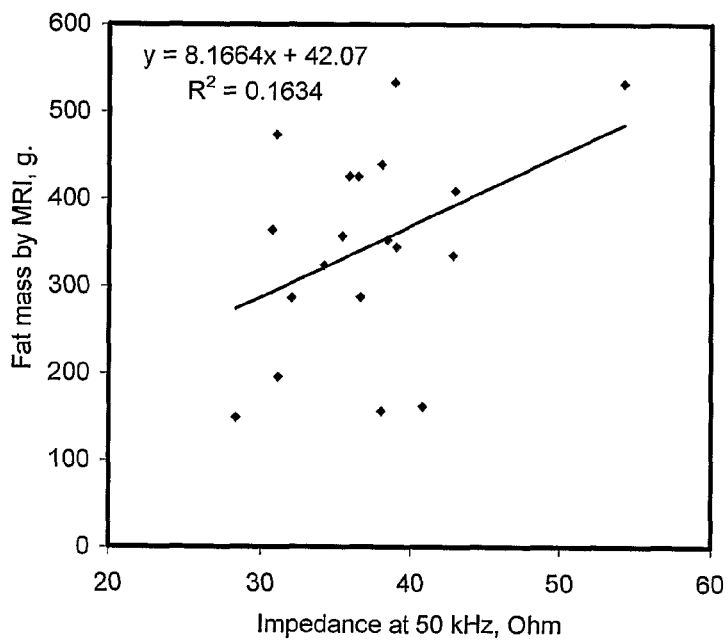

Comparative Example Multi-Frequency, Three Parallel Path Model Versus 50 Kilohertz FIGS. 14 and 15 compare correlations between bioimpedance and MRI measurements achieved using the multi-frequency, three parallel path model of FIG. 2 with correlations achieved using impedance at a single frequency, namely, the commonly used frequency of 50 kilohertz. The data used in preparing these figures was the data discussed above in connection with Examples 1 and 2.

FIG. 14 shows muscle mass correlations, while FIG. 15 shows fat mass correlations. As illustrated by these figures, the multi-frequency, three parallel path equivalent circuit frequency response model of the invention achieves higher correlations than the single 50 kilohertz approach both for muscle mass ($R^2$ of 0.6 for the invention versus 0.3 for 50 kilohertz) and for fat mass ($R^2$ of 0.7 for the invention versus 0.2 for 50 kilohertz).

Example 5

Figure 16A:
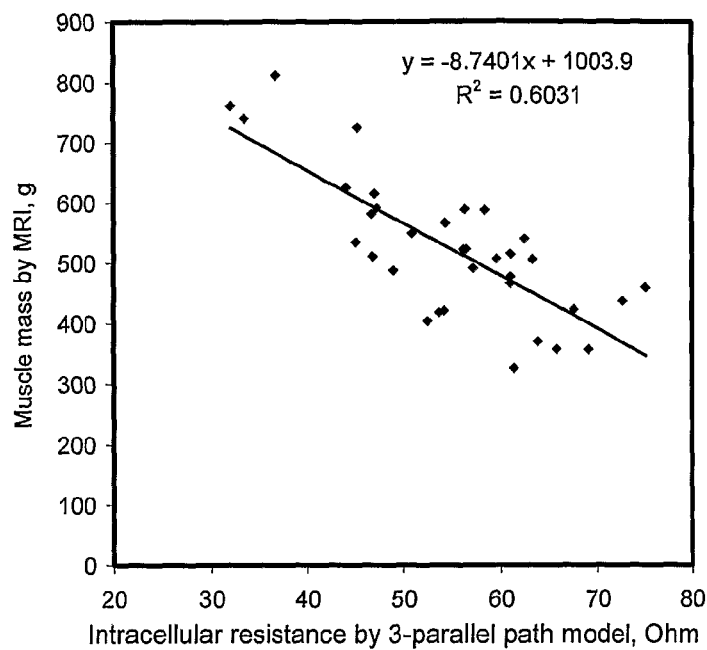
FIG. 16 compares (i) a correlation between muscle mass measured by MRI and intracellular resistance ($R_I$) determined using the multi-frequency, three parallel path model of the invention (FIG. 16A) with (ii) a correlation between muscle mass measured by MRI and intracellular resistance determined using the Cole-Cole model (FIG. 16B).
Figure 16B:
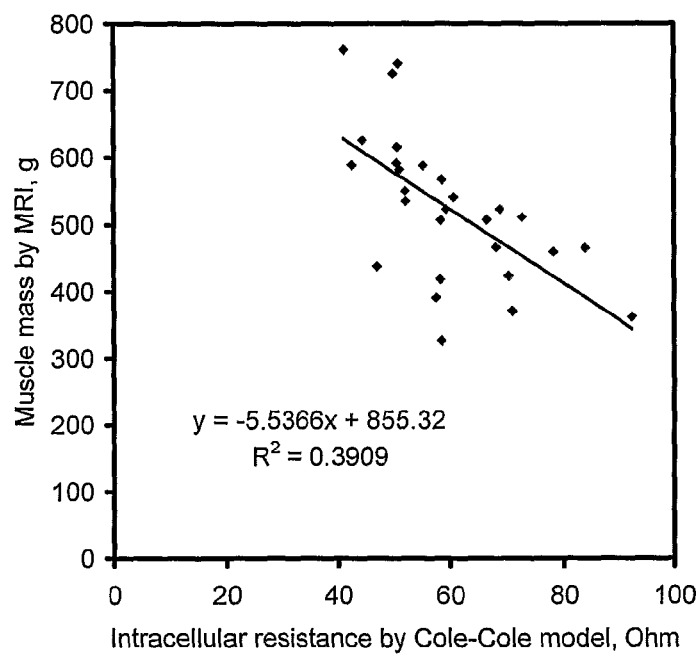
Figure 17A:
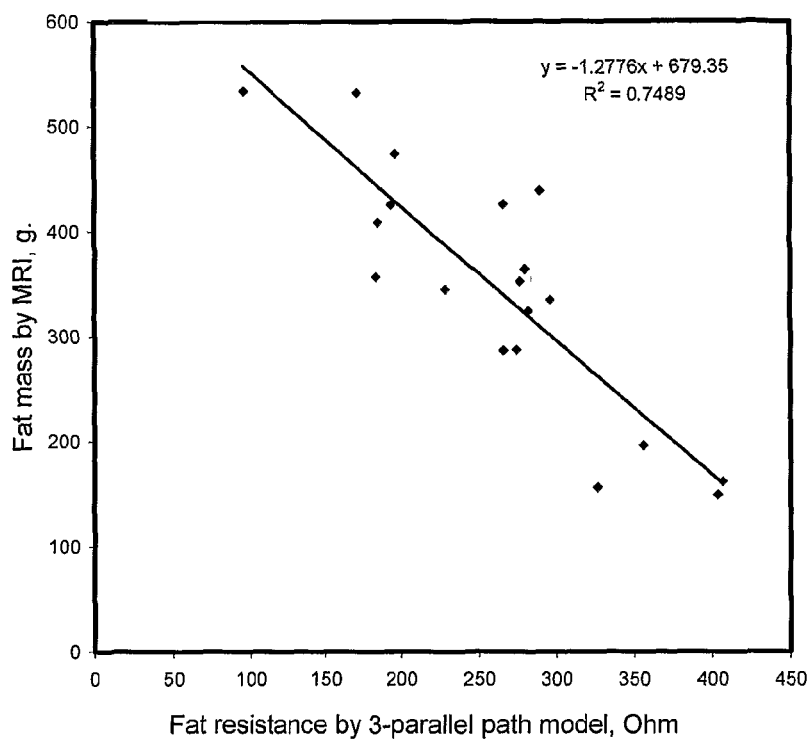
FIG. 17 compares (i) a correlation between fat mass measured by MRI and fat resistance ($R_F$) determined using the multi-frequency, three parallel path model of the invention (FIG. 17A) with (ii) a correlation between fat mass measured by MRI and intracellular resistance determined using the Cole-Cole model (FIG. 17B).
Figure 17B:
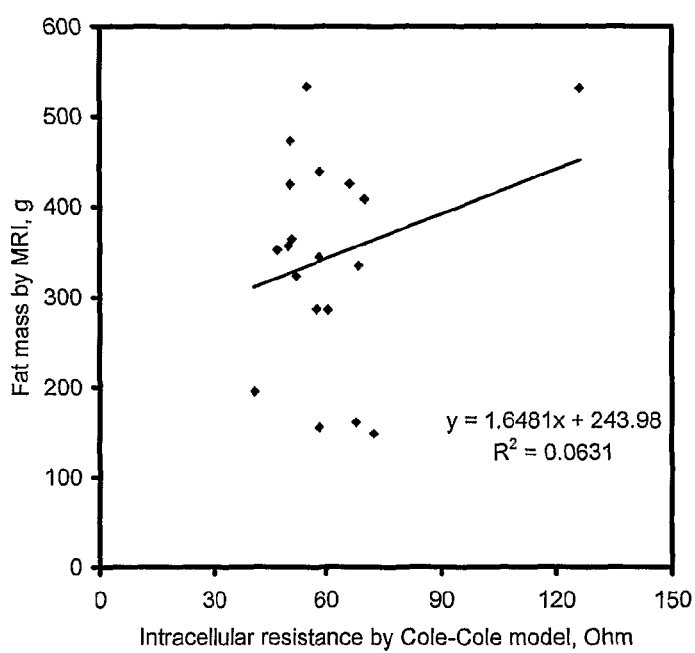

Comparative Example Multi-Frequency, Three Parallel Path Model Versus Cole-Cole Model FIGS. 16 and 17 compare correlations between BIS and MRI measurements achieved using the multi-frequency, three parallel path model of FIG. 2 with correlations achieved using the Cole-Cole model. The data used in preparing these figures was the data discussed above in connection with Examples 1 and 2.

FIG. 16 shows muscle mass correlations, while FIG. 17 shows fat mass correlations. As illustrated by these figures, the multi-frequency, three parallel path equivalent circuit frequency response model of the invention achieves higher correlations than the Cole-Cole model both for muscle mass ($R^2$ of 0.6 for the invention versus 0.4 for the Cole-Cole model) and for fat mass ($R^2$ of 0.7 for the invention versus 0.1 for the Cole-Cole model).

Although specific embodiments of the invention have been described and illustrated, it is to be understood that a variety of modifications which do not depart from the scope and spirit of the invention will be evident to persons of ordinary skill in the art from the foregoing disclosure. As just one example, although the following claims recite various features of the invention, it is to be understood that the invention encompasses any and all combinations of those features, irrespective of whether such combination is currently set forth in the appended set of claims.

REFERENCES

Citations for the various documents referred to above are set forth below. The contents of these documents are incorporated herein by reference.

[1] K. S. Cole and R. H. Cole, "Dispersion and absorption in dielectrics. I. Alternating current characteristics" J. chem. Phys. Vol. 9, pp. 341-351, 1941

[2] H. P. Schwan, K. Li, "A dielectric study of the low-conductance surface membrane," in E. coli Nature Vol. 177, pp. 134-135, 1956

[3] J. Nyboer, Electrical impedance plethysmography, $2^{nd}$ ed., Charles C. Thomas, Springfield, Ill. 1970

[4] R. P. Patterson, "Fundamentals of impedance cardiography," IEEE Engineering in Medicine and Biology magazine. Vol. 8, pp. 16-18, 1989

[5] T. Hanai, Electrical properties of emulsions In: Emulsion Science, edited by P. H. Sherman London: Academic, 1968, pp. 354-477,

[6] A. De Lorenzo, A. Andreoli, J. R. Matthie, and P. O. Withers, "Predicting body cell mass with bioimpedance by using theoretical methods: a technological review," J Appl Physiol Vol. 82, pp. 1542-1558, 1997

[7] R. N. Baumgartner, R. Ross and S. B. Heymsfield, "Does adipose tissue influence bioelectric impedance in obese men and women?" J. Appl. Physiol. Vol. 84, pp. 257-262, 1998.

[8] K. R. Foster and H. C. Lukaski, "Whole-body impedance-what does it measure?" Am J Clin Nutr Vol. 64 (suppl), pp. 388S-396S, 1996

[9] F. Zhu, S. Sarkar, C. Kaitwatcharachai, R. Greenwood, C. Ronco, N. W. Levin, "Methods and reproducibility of measurement of resistivity in the calf using regional bioimpedance analysis. Blood Purif," Vol. 21, pp. 131-136, 2003

[10] Xitron Technologies, Inc., "4000B Bio-Impedance Spectrum Analyzer System Operating Manual," preliminary edition, San Diego, Calif., 1995, Appendix A, pages 50-61.

TABLE 1

|  | Permittivity $\epsilon$ | Resistivity $\rho$ ($\Omega$-cm) |
|---|---|---|
| Bone | 640 | $10^4$ |
| Fat | $3 \times 10^4$ | $1.5 \sim 5 \times 10^3$ |
| Blood | $2.8 \times 10^3$ | $1.5 \times 10^2$ |
| Muscle (parallel) | $8 \times 10^4$ | $2 \times 10^2$ |

TABLE 2

SUBJECT INFORMATION

|  | Mean | SD | min | max |
|---|---|---|---|---|
| SEX | F9/M19 |  |  |  |
| AGE, year | 53.4 | 10.5 | 33 | 69 |
| WEIGHT, kg | 80.4 | 18 | 43.2 | 119.9 |
| Height, cm | 169.7 | 9.5 | 149 | 184.9 |
| BMI, kg/m2 | 27.7 | 4.97 | 19.18 | 41.11 |
| FAT, g | 344.9 | 118 | 149.2 | 533.5 |
| MUSCLE, g | 525.3 | 110.3 | 326.5 | 761.5 |

TABLE 3

| VF/VG | $\rho G$, Mea ($\Omega$-cm) | $\rho^*G$, Cal ($\Omega$-cm) | $\rho G$, Cal ($\Omega$-cm) | $\Delta\rho$ ($\Omega$-cm) |
|---|---|---|---|---|
| >0.2 | 430.4 ± 62 | 359.9 ± 43 | 457.2 ± 64 | 70.5 ± 24 |
| =<0.2 | 369.5 ± 84 | 322.7 ± 57 | 373.5 ± 70 | 46.8 ± 29 |
| p value | <0.05 | n.s. | <0.005 | <0.05 |

$\rho_{G, Cal}$ and $\rho^*_{G, Cal}$ are the resistivity values calculated using Eq. 12 and Eq. 13, respectively; $\Delta\rho = \rho_{G, Mea} - \rho^*_{G, Cal}$; a $\rho_E$ value of 90 $\Omega$·cm was used in calculating $\rho^*_{G, Cal}$ and $\rho_{G, Cal}$.

TABLE 4

| | SUMMARY OF PARAMETERS FROM CURVE FITTING | | | | | | |
|---|---|---|---|---|---|---|---|
| Fat | P1 | P2 | P3 | P4 | Q1 | Q2 | Q3 |
| G1 | 32.54 ± 5.9 * | 1412 ± 262 | −15330 ± 3352 | 42640 ± 12130 + | 22.5 ± 6.7 | −276.4 ± 76 | 649.8 ± 430 |
| G2 | 27.3 ± 3.7 * | 1187 ± 548 | −13012 ± 3027 | 34166 ± 13808 | 22.6 ± 7.7 | −262 ± 73 | 718 ± 372 |
| G3 | 26 ± 4.4 | 1168 ± 259 | −10973 ± 3448 | 24191 ± 16426 + | 20.7 ± 8.7 | −197.2 ± 102 | 460.3 ± 460 |

* and + indicate a significant (p < 0.05) difference between groups.

What is claimed is:

1. A method for determining the circumference of a portion of a body segment covered by skin comprising:
   (a) applying a series of electrodes around said portion, said series of electrodes having a first electrode and a last electrode, the circumferential distances between all electrodes in the series being known, except for the distance between the first and last electrodes;
   (b) determining the resistance between at least two electrodes of the series, other than the first and last electrode, by applying a low frequency current which does not substantially penetrate the skin;
   (c) determining a resistivity value per unit length for the skin from the resistance determined in step (b) and the known circumferential distance between the two electrodes;
   (d) determining the resistance between the first and last electrodes of the series by applying a low frequency current which does not substantially penetrate the skin; and
   (e) calculating the distance between the first and last electrodes of the series from the resistance measured in step (d) and the resistivity value per unit length determined in step (c).

2. The method of claim 1 wherein the resistances between all adjacent pairs of electrodes, other than the first and last electrodes, are determined in step (b) and used in step (c) to determine the resistivity value.

3. The method of claim 1 wherein, except for the first and last electrodes, the distances between adjacent pairs of electrodes are equal.

4. The method of claim 1 wherein the series of electrodes are carried by a belt.

5. Apparatus comprising a programmed computer for determining the circumference of a portion of a body segment covered by skin, said apparatus being adapted for use with a series of electrodes for application around said portion of a body segment, said series of electrodes having a first electrode and a last electrode, the circumferential distances between all electrodes in the series being known, except for the distance between the first and last electrodes, said programmed computer comprising a non-transitory computer readable storage medium having computer executable code embodied therein for performing the steps of:
   (i) determining the resistance between at least two electrodes of the series of electrodes, other than the first and last electrode, by applying a low frequency current which does not substantially penetrate the skin;
   (ii) determining a resistivity value per unit length for the skin from the resistance determined in step (i) and the known circumferential distance between the two electrodes;
   (iii) determining the resistance between the first and last electrodes of the series by applying a low frequency current which does not substantially penetrate the skin; and
   (iv) calculating the distance between the first and last electrodes of the series from the resistance determined in step (iii) and the resistivity value per unit length determined in step (ii).

* * * * *